United States Patent [19]

Leavitt et al.

[11] 4,363,286
[45] Dec. 14, 1982

[54] FINGER-PRINTING PACKET

[75] Inventors: Larry J. Leavitt, 3854 S. Parkway #3A, Northbrook, Ill. 60062; John E. Madigan, Arvada, Colo.

[73] Assignee: Larry Leavitt, Northbrook, Ill.

[21] Appl. No.: 273,228

[22] Filed: Jun. 12, 1981

[51] Int. Cl.³ .............................................. B41K 1/00
[52] U.S. Cl. ...................................... 118/31.5; 427/1
[58] Field of Search .......................... 118/31.5; 427/1; 53/412

[56] References Cited

U.S. PATENT DOCUMENTS

| | | | |
|---|---|---|---|
| 3,054,679 | 9/1962 | Bradford | 53/412 |
| 3,089,459 | 5/1963 | Picard | 118/31.5 |
| 3,664,910 | 5/1972 | Hollie | 118/31.5 |
| 3,709,524 | 1/1973 | McKee et al. | 118/31.5 |
| 3,720,304 | 3/1973 | Laugherty et al. | 118/31.5 |

Primary Examiner—James R. Hoffman

[57] ABSTRACT

This finger-printing packet consists primarily of an inked sheet, for placement in a suitable jig, to apply ink to a person's finger, so as to obtain excellent finger-prints on a finger-print form. It further includes a foil cover, suitably adhered to the inked surface of the sheet, and a corner tab enables the user to remove the foil cover from the sheet easily.

1 Claim, 5 Drawing Figures

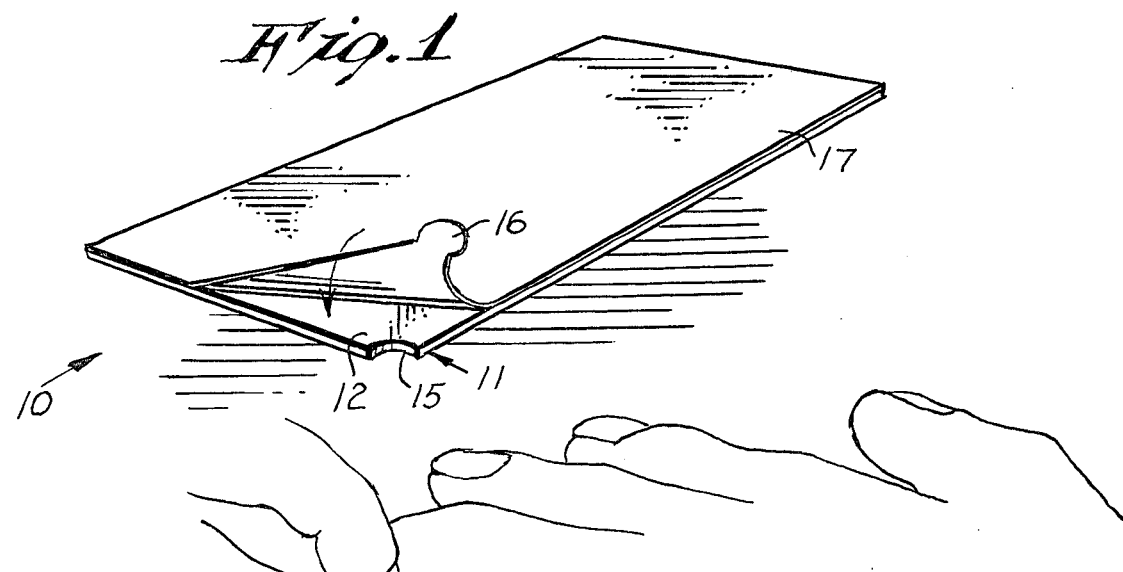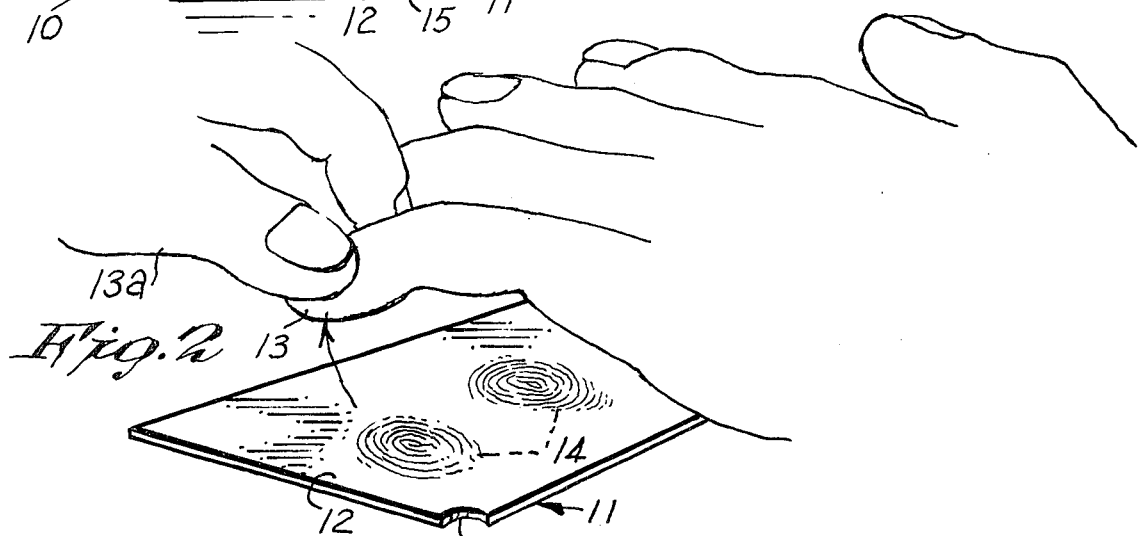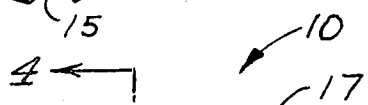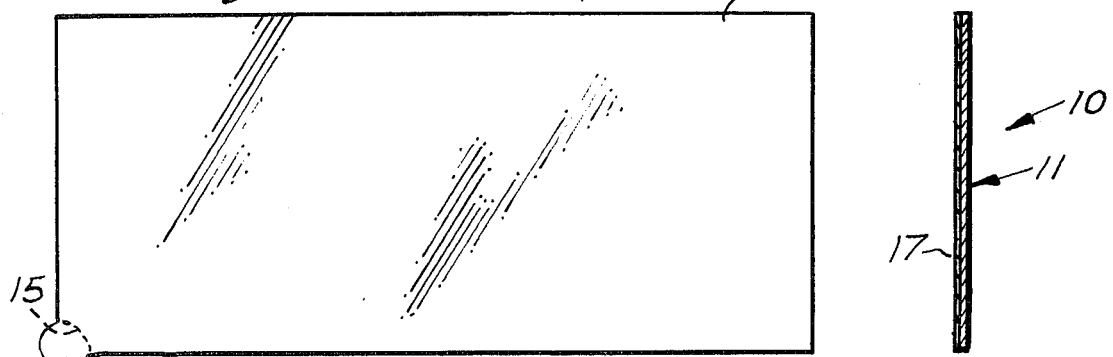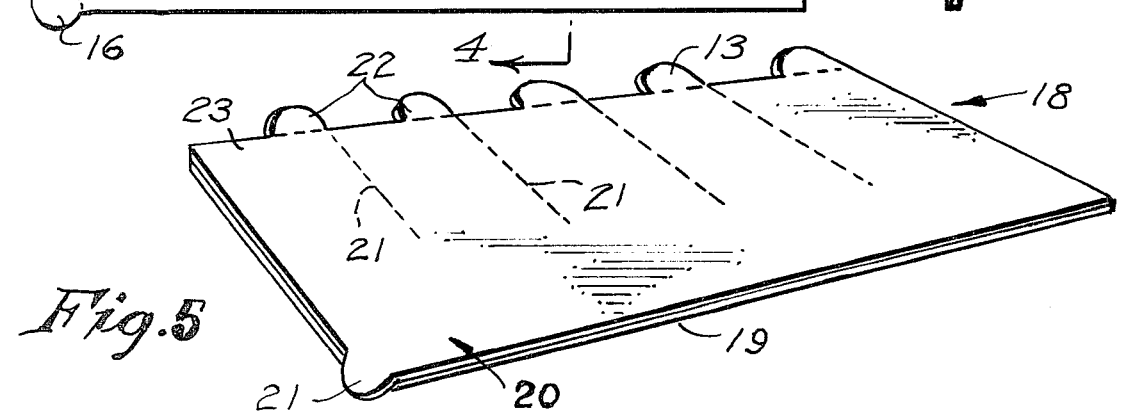

FINGER-PRINTING PACKET

This invention relates to printing devices, and more particularly, to a finger-printing packet.

It is, therefore, the principal object of this invention to provide a finger-printing packet, which will eliminate the standard procedure of finger-printing employed by law enforcement agencies, which is the use of a tube of ink and a roller, in the attempt to obtain the proper amount of ink on a metal surface, to create a good set of finger-prints.

It is well known, that if the ink used is too thick, it will create a poor set of finger-prints, and any prints that cannot be used, are sent back to local police departments, by the Federal Bureau of Investigation.

Another object of this invention is to provide a finger-printing packet, which will enable a law enforcement officer to obtain finger-prints much faster than was possible in the prior art.

Another object of this invention is to provide a finger-printing packet, which will always have the proper amount of ink, so as to enable the finger-prints taken to be consistently excellent in quality.

A further object of this invention is to provide a finger-printing packet, which will fit into a jig, so as to enable an officer to tear away the top portion of the packet, to expose the inked surface.

Other objects are to provide a finger-printing packet, which is simple in design, inexpensive to manufacture, rugged in construction, easy to use, and efficient in operation.

These, and other objects, will be readily evident, upon a study of the following specification, and the accompanying drawing, wherein:

FIG. 1 is a perspective view of the present invention, showing the top foil covering partially peeled away;

FIG. 2 is a perspective view of FIG. 1, showing the top foil covering removed therefrom, and illustrates the invention in use;

FIG. 3 is a top plan view of the invention, showing the foil covering intact;

FIG. 4 is a cross-sectional view, taken along the line 4—4 of FIG. 3, and

FIG. 5 is a perspective view of a modified form of the invention.

According to this invention, a packet 10 is shown to include a rectangular sheet 11, having an inked top surface 12, for the placement of a person's fingers 13, to obtain clear finger-prints 14. An arcuate cut-out 15, in one corner of sheet 11, is covered by means of a projecting finger tab 16, so as to enable the user to easily remove the foil cover 17 from the inked top surface 12.

In use, the packet 10 is placed in a suitable jig (not shown), and the tab 16 is grasped by the user's fingers 13a, and is pulled up, thus removing the foil cover 17 from the inked surface 12, so as to obtain finger-prints 14.

Referring now to FIG. 5 of the drawing, a modified form 18 is shown to include an inked sheet 19, having a foil cover 20. The foil cover 20 includes a tab 21, similar to that of packet 10, for removing the entire cover 20, so as to finger-print a five-fingered hand. Foil cover 20 also includes perforation lines 21, which terminate at an individual tab 22, so as to peel off strips 23 selectively, to finger-print a hand having some fingers missing.

In use, packet 18 is used in the same aforementioned manner, as described of packet 10, with the exception, that packet 18 includes a plurality of strips 23, defined by the partial perforation lines 21.

As clearly shown in FIG. 5, all the tabs 22 are located along a side edge, which is opposite a side edge having the tab 21 at its one corner. Also, the perforation lines, beginning at the tabs 22, extend only a partial distance across the foil, so that this portion of the foil permits only segmented strips 23 thereof to be individually lifted from the inked sheet 19. After the selected strip is raised to the full extent of the perforations at each side edge thereof, a continuing upward pull of the strip will result in a rough tear commencing from the perforations and extending to the foil opposite edge, so as to remove completely the torn off strip. However, when the tab 21 is pulled, then the entire unperforated opposite portion of the foil is lifted, and a continuing pull then lifts the foil portion having the rows of perforations, so that the entire foil is removed in one piece by means of a singular pull.

While various changes may be made in the detail construction, it is understood that such changes will be within the spirit and scope of the present invention, as is defined by the appended claims.

What we now claim is:

1. A fingerprinting packet, comprising, in combination, a rectangular-shaped, inked sheet, against which fingers are impressed so as to form fingerprints thereupon, and a same-shaped foil cover adhered to an inked side thereof, an arcuate cut-out at one corner of said inked sheet, a projecting finger tab on a corresponding corner of said foil cover; said finger tab being at a corner of a first side edge of said foil cover which is opposite a foil second side edge having a plurality of spaced-apart tabs, a row of perforations at each said tab which is along said second edge, each said row of perforations extending at right angles from said second edge and partially across said foil cover, so as to form foil strips therebetween.

* * * * *